(12) United States Patent
Hsiao et al.

(10) Patent No.: US 8,252,896 B2
(45) Date of Patent: Aug. 28, 2012

(54) PROCESS FOR MAKING BIVALIRUDIN

(75) Inventors: Tsung Yu Hsiao, Kaohsiung County (TW); Jin Guo Ding, Shanghai (CN); Hung Wei Chuang, Tainan County (TW)

(73) Assignee: ScnioPharm Taiwan, Ltd., Tainan (TW)

( * ) Notice: Subject to any disclaimer, the term of this patent is extended or adjusted under 35 U.S.C. 154(b) by 125 days.

(21) Appl. No.: 12/553,482

(22) Filed: Sep. 3, 2009

(65) Prior Publication Data

US 2010/0056755 A1    Mar. 4, 2010

Related U.S. Application Data

(60) Provisional application No. 61/190,928, filed on Sep. 3, 2008.

(51) Int. Cl.
| A61K 38/00 | (2006.01) |
| A61K 38/04 | (2006.01) |
| C07K 5/00  | (2006.01) |
| C07K 7/00  | (2006.01) |
| C07K 16/00 | (2006.01) |
| C07K 17/00 | (2006.01) |

(52) U.S. Cl. .................. 530/326; 530/329; 530/330

(58) Field of Classification Search ................. None
See application file for complete search history.

(56) References Cited

U.S. PATENT DOCUMENTS

| 5,196,404 | A | 3/1993 | Maraganore et al. |
| 5,240,913 | A | 8/1993 | Maraganore et al. |
| 5,425,936 | A | 6/1995 | Maraganore et al. |
| 5,433,940 | A | 7/1995 | Maraganore et al. |
| 5,514,409 | A | 5/1996 | Maraganore et al. |
| 5,691,311 | A | 11/1997 | Maraganore et al. |
| 2007/0093423 | A1* | 4/2007 | Tovi et al. .................. 514/13 |
| 2007/0213505 | A1* | 9/2007 | Epstein et al. ............. 530/331 |
| 2008/0051558 | A1 | 2/2008 | Zhou |
| 2008/0287648 | A1 | 11/2008 | Droz et al. |
| 2008/0287650 | A1 | 11/2008 | Tovi et al. |
| 2009/0062511 | A1 | 3/2009 | Palle et al. |

FOREIGN PATENT DOCUMENTS

WO    WO 98/50563    11/1998

OTHER PUBLICATIONS

International Search Report and Written Opinion dated Nov. 30, 2009.

* cited by examiner

*Primary Examiner* — Cherie M Stanfield

(57) ABSTRACT

The present invention relates to the efficient commercial synthesis of Bivalirudin.

7 Claims, 5 Drawing Sheets

Preparation of S1

PROCESS FOR MAKING BIVALIRUDIN

RELATED APPLICATIONS

This application claims priority from U.S. Provisional Patent Application Ser. No. 61/190,928 which was filed on Sep. 3, 2008. The entire content of which is herein incorporated by reference.

BACKGROUND OF THE INVENTION

1. Field of the Invention

The present invention relates to the efficient commercial synthesis for the making of bivalirudin, a peptide. It is well known that bivalirudin is indicated to reduce the risk of acute ischemic complications, and is an anticoagulant and acts as a direct thrombin inhibitor. The process substantially comprises the syntheses of various fragments of the polypeptide and the coupling of the fragments to produce bivalirudin.

2. Description of the Related Arts

Thrombin inhibitors are synthesized by various techniques which are well known in the art. These include enzymatic cleavage of natural or recombinant hirudin, recombinant DNA techniques, solid-phase peptide synthesis, solution-phase peptide synthesis, organic chemical synthesis techniques, or a combination of these techniques.

The following references disclose various techniques for producing thrombin inhibitors.
(1) U.S. Pat. No. 5,196,404
(2) U.S. Pat. No. 5,240,913
(3) U.S. Pat. No. 5,425,936
(4) U.S. Pat. No. 5,433,940
(5) U.S. Pat. No. 5,514,409
(6) U.S. Pat. No. 5,691,311
(7) US 2007093423
(8) US 2008051558
(9) US 2008287648
(10) US 2008287650
(11) US 20090062511
(12) WO9850563

The disclosure of the above references are herein incorporated in their entirety by reference. Certain of the references disclose the solid-phase peptide synthesis for making Bivalirudin, as the synthesis can be rapidly conducted. However, this synthesis method results in low yield and high cost of manufacture.

SUMMARY OF THE INVENTION

The present invention provides for an efficient process of making Bivalirudin in solution that is high in yield and scalable for commercial production. The process comprises the stepwise synthesis of amino acid segments S1, S2, S3, S4, and the coupling together of these segments to produce Bivalirudin. The process of the present invention provides for the making of Bivalirudin that is in high yield and of high purity compared to the solid-phase peptide synthesis method.

The appended claims are directed to process for making Bivalirudin and for making various novel intermediates. Recitation within these claims to first organic solvent, second organic solvent, and so forth, is meant to indicate that the organic solvents may be different or the same within the same claimed process; and that recitation of the same term for the organic solvent from one claimed process to another different claimed process does not necessarily indicate that the solvents are the same.

BRIEF DESCRIPTION OF THE DRAWINGS

FIG. 2 discloses "S2M3" as SEQ ID NO: 1, "S2" as SEQ ID NO: 2, "S2M5" as SEQ ID NO: 2 and "S2M4" as SEQ ID NO: 1, respectively.

FIG. 3 discloses "S3M7" as SEQ ID NO: 4, "S3M6" as SEQ ID NO: 3, "S3M5" as SEQ ID NO: 3, "S3M8" as SEQ ID NO: 4, "S3M9" as SEQ ID NO: 5 and "S3" as SEQ ID NO: 5, respectively.

FIG. 4 discloses "S4" and "S4M5" as SEQ ID NO: 6.

FIG. 5 discloses "S2" as SEQ ID NO: 2, "S3" as SEQ ID NO: 5, "M1" as SEQ ID NO: 7, "M2" as SEQ ID NO: 7, "S4" as SEQ ID NO: 6 and "Bivalirudin" as SEQ ID NO: 8, respectively.

DETAILED DESCRIPTION OF THE PRESENTLY PREFERRED EMBODIMENTS

Figure 1:
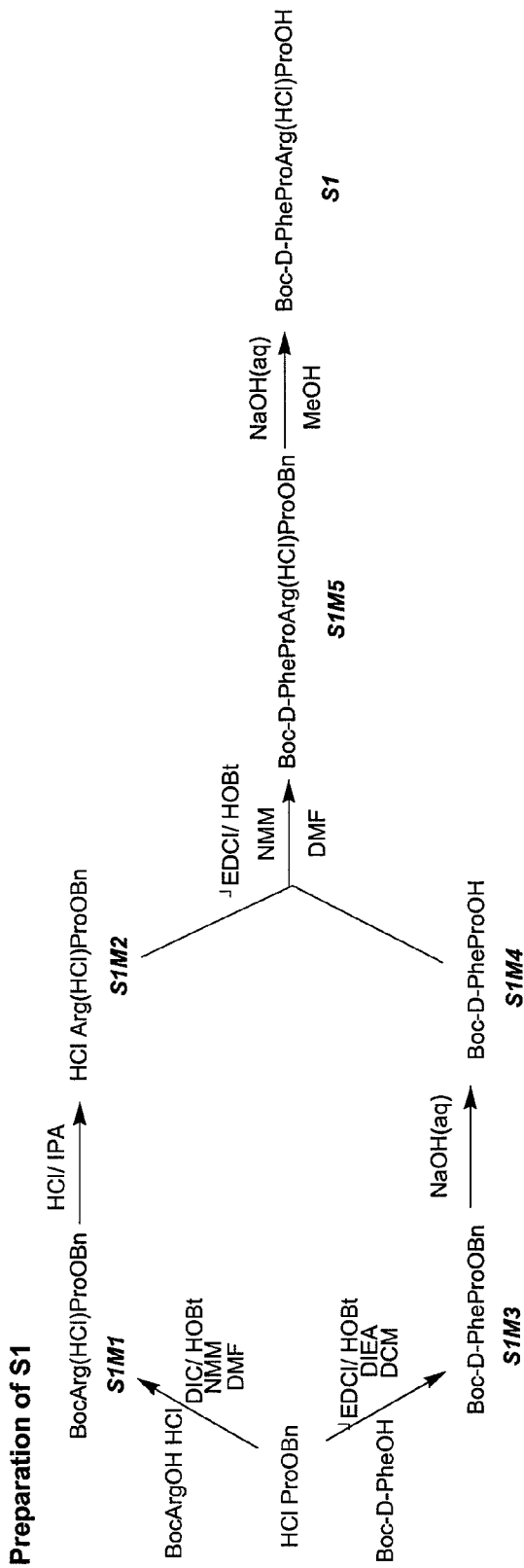
FIG. 1 depicts the synthesis of the peptide Segment 1 (S1) as disclosed in Examples 1, 2 and 3.
Figure 2:
FIG. 2 depicts the synthesis of the peptide Segment 2 (S2) as disclosed in Examples 4 and 5.
Figure 3:
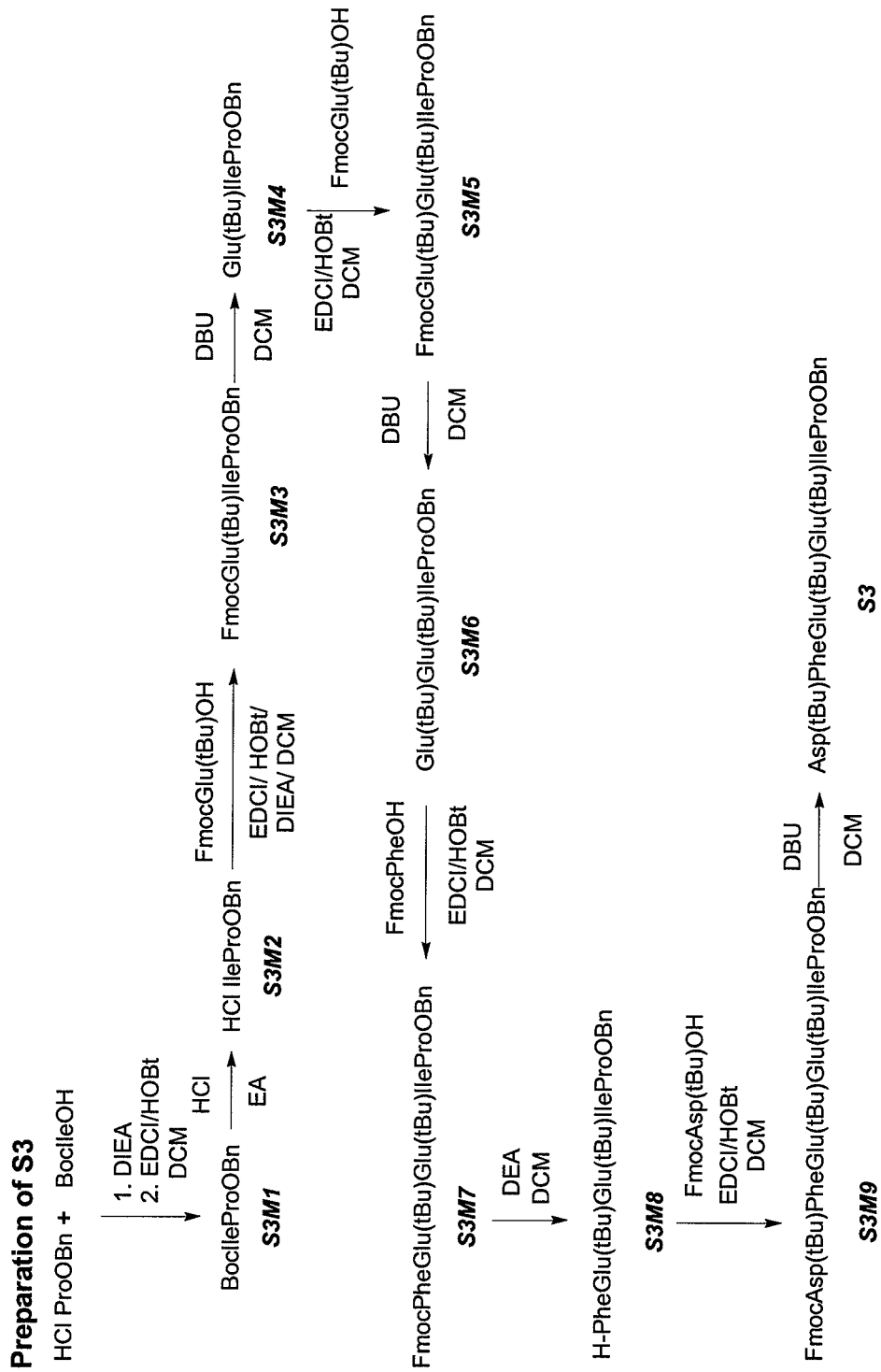
FIG. 3 depicts the synthesis of the peptide Segment 3 (S3) as disclosed in Examples 6, 7 and 8.
Figure 4:
FIG. 4 depicts the synthesis of the peptide Segment 4 (S4) as disclosed in Examples 9 and 10.
Figure 5:
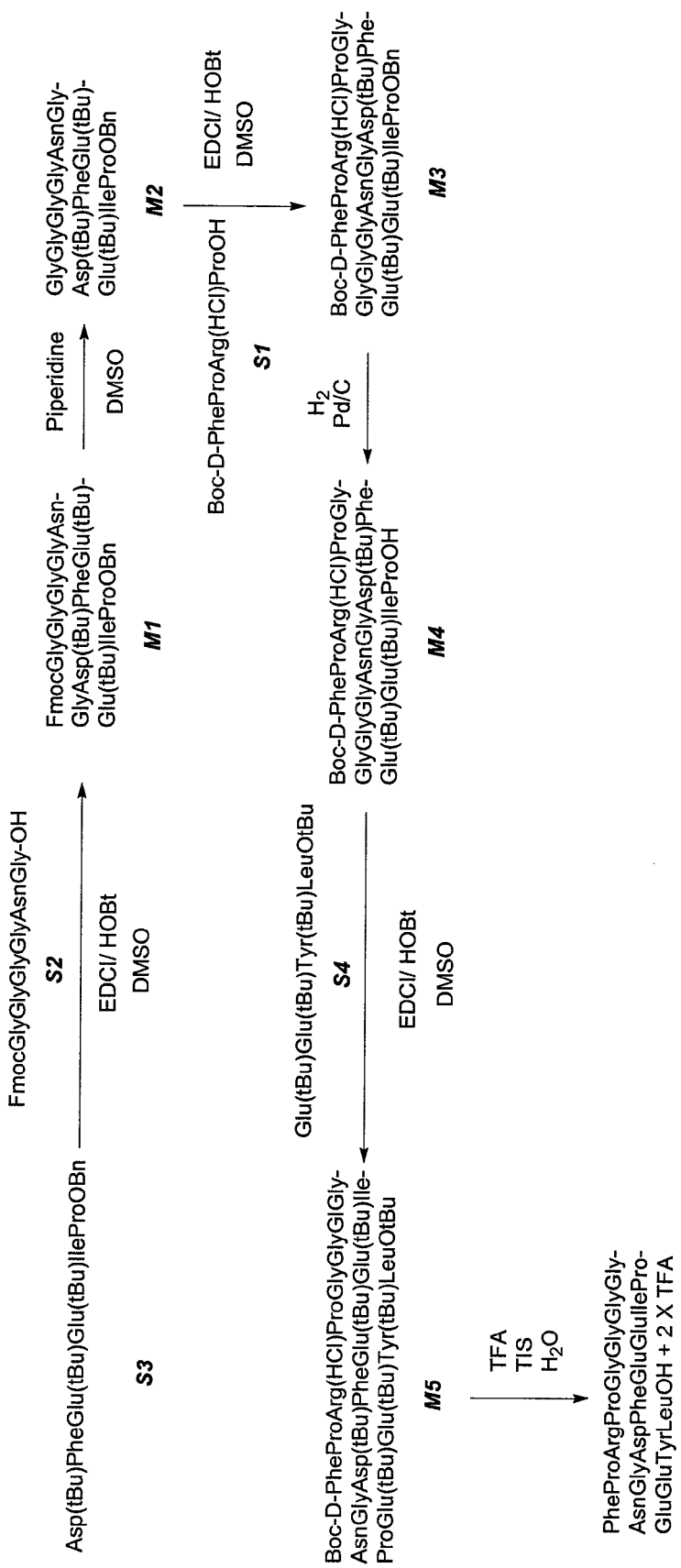
FIG. 5 depicts the synthesis of the Bivalirudin as disclosed in Examples 11, 12 and 13.

The identifying reference codes of the intermediates used in the present description and schemes are defined as follows.
S1M1 (M1 of segment 1)—BocArg(HCl)ProOBn
S1M2 (M2 of segment 1)—HCl Arg(HCl)ProOBn
S1M3 (M3 of segment 1)—Boc-D-PheProOBn
S1M4 (M4 of segment 1)—Boc-D-PheProOH
S1M5 (M5 of segment 1)—Boc-D-PheProArg(HCl)ProOBn
S1 (Segment 1)—Boc-D-PheProArg(HCl)ProOH
S2M1 (M1 of segment 2)—FmocAsn(Trt)GlyOtBu
S2M2 (M2 of segment 2)—Asn(Trt)GlyOtBu
S2M3 (M3 of segment 2)—FmocGlyAsn(Trt)GlyOtBu
S2M4 (M4 of segment 2)—GlyGlyAsn(Trt)GlyOtBu (SEQ ID NO: 1)
S2M5 (M5 of segment 2)—FmocGlyGlyGlyGlyAsn(Trt)GlyOtBu (SEQ ID NO: 2)
S2 (Segment 2)—FmocGlyGlyGlyGlyAsnGlyOH (SEQ ID NO: 2)
S3M1 (M1 of segment 3)—BocIleProOBn
S3M2 (M2 of segment 3)—HCl IleProOBn
S3M3 (M3 of segment 3)—FmocGlu(tBu)IleProOBn
S3M4 (M4 of segment 3)—Glu(tBu)IleProOBn
S3M5 (M5 of segment 3)—FmocGlu(tBu)Glu(tBu)IleProOBn (SEQ ID NO: 3)
S3M6 (M6 of segment 3)—Glu(tBu)Glu(tBu)IleProOBn (SEQ ID NO: 3)
S3M7 (M7 of segment 3)—FmocPheGlu(tBu)Glu(tBu)IleProOBn (SEQ ID NO: 4)
S3M8 (M8 of segment 3)—H-PheGlu(tBu)Glu(tBu)IleProOBn (SEQ ID NO: 4)
S3M9 (M9 of segment 3)—FmocAsp(tBu)PheGlu(tBu)Glu(tBu)IleProOBn (SEQ ID NO: 5)
S3 (Segment 3)—Asp(tBu)PheGlu(tBu)Glu(tBu)IleProOBn (SEQ ID NO: 5)
S4M1 (M1 of segment 4)—FmocTyr(tBu)LeuOtBu
S4M2 (M2 of segment 4)—Tyr(tBu)LeuOtBu
S4M3 (M3 of segment 4)—FmocGlu(tBu)Tyr(tBu)LeuOtBu
S4M4 (M4 of segment 4)—Glu(tBu)Tyr(tBu)LeuOtBu
S4M5 (M5 of segment 4)—FmocGlu(tBu)Glu(tBu)Tyr(tBu)LeuOtBu (SEQ ID NO: 6)

S4 (Segment 4)—Glu(tBu)Glu(tBu)Tyr(tBu)LeuOtBu (SEQ ID NO: 6)

M1—Fmoc-GlyGlyGlyGlyAsnGlyAsp(tBu)PheGlu(tBu)Glu(tBu)IleProOBn (SEQ ID NO: 7)

M2—GlyGlyGlyGlyAsnGlyAsp(tBu)PheGlu(tBu)Glu(tBu)IleProOBn (SEQ ID NO: 7)

M3—Boc-D-PheProArg(HCl)ProGlyGlyGlyGlyGlyAsnGlyAsp(tBu)—PheGlu(tBu)Glu(tBu)IleProOBn

M4—Boc-D-PheProArg(HCl)ProGlyGlyGlyGlyGlyAsnGlyAsp(tBu)—PheGlu(tBu)Glu(tBu)IleProOH

M5—Boc-D-PheProArg(HCl)ProGlyGlyGlyGlyGlyAsnGlyAsp(tBu)—PheGlu(tBu)Glu(tBu)IleProGlu(tBu)Glu(tBu)Tyr(tBu)LeuOtBu

The abbreviations used in the present description are defined as follows.

Boc—tert-Butyloxycarbonyl
Bn—benzyl
Fmoc—9-Fluorenylmethyloxycarbonyl
Trt—Trityl
tBu—tert-Butyl
HOBt—N-hydroxybenzotriazole
EDCl—Ethyl(3-dimethylaminopropyl)carbodiimide hydrochloride
EA—Ethyl acetate
DIC—N,N'-Diisopropylcarbodiimide
DCM—Dichloromethane
DMF—N,N-Dimethylformamide
DMSO—Dimethyl sulfoxide
DBU—1,8-Diazobicyclo[5,4,0]undec-7-ene
DEA—Diethanolamine
DIEA—N,N-Diisoproylethylamine
MTBE—Methyl tert-butyl ether
NMM—N-Methylmorpholine The following examples are provided for the purpose of further illustration only and are not intended to be limitations on the disclosed invention.

Example 1

Preparation of HCl Arg(HCl)ProOBn (S1M2)

The protected amino acid BocArgOH.HCl.H2O (1.00 Kg) and ProOBn.HCl (0.77 kg) were dissolved in DMF (3 L) and HOBt (0.45 kg) was added. DIC (0.57 L) and NMM (0.37 L) were added and the reaction was stirred for another 15 h. The reaction mixture was filtered and the intermediate was precipitated out by addition of Acetone (30 L). The precipitated intermediate (S1M1) was separated by filtration and washed with Acetone (2×6 L). The precipitated intermediate (S1M1) was dissolved in HCl(g)/IPA (13%, 5 L) and the reaction was stirred for 6 h. The product was precipitated out by added into pre-cooled methyl-t-butyl ether (MTBE, 40 L). The precipitated product was separated by filtration and washed with MTBE (2×20 L). Yield: 1.06 Kg Example 2

Preparation of Boc-D-PheProOH (S1M4)

The protected amino acid Boc-D-PheOH (1.00 Kg) and ProOBn.HCl (0.93 kg) were dissolved in DCM (8 L) and HOBt (0.56 kg) was added. DIEA (0.72 L) and EDCl (0.87 kg) were added and reaction was stirred for 2 h. The reaction mixture was washed with 5% sodium bicarbonate solution (10 L), 2.5% Citric acid solution (5 L) and 5% sodium bicarbonate solution (5 L) and was concentrated to get intermediate of yellow oil (S1M3). The intermediate (S1M3) was cooled to 20° C. and 1N NaOH (aq. 7.5 L) was added. The reaction mixture was allowed to assume room temperature for another 3 h. The reaction mixture was neutralized with 1 N HCl (aq.), followed by concentrated to about 3/5 volume. The product in aqueous layer was precipitated out by adjusting pH to about 3 with 1N HCl (aq.). The precipitated product was separated by filtration and washed with water (2×10 L). Yield: 1.12 Kg Example 3

Preparation of Boc-D-PheProArg(HCl)ProOH (S1)

The compounds from Example 1 (1.00 Kg) and Example 2 (1.32 kg) were dissolved in DMF (5 L) and HOBt (0.41 kg) was added. NMM (0.41 L) and EDCI (0.63 kg) were added and the reaction was stirred for 2 h. The reaction mixture was diluted by DCM (10 L), washed with water (10 L) and concentrated to about 1/5 volume. The concentrated mixture was added into methyl-t-butyl ether (MTBE, 40 L) for intermediate precipitation. The precipitated intermediate was separated by filtration and washed with MTBE (2×20 L) to get intermediate (S1M5). The intermediate (S1M5) was dissolved in MeOH (6 L) followed by added into mixed solvents of MeOH (6 L) and 1N NaOH (aq. 5.5 L). The reaction was allowed stirring for 5 h, then neutralized with HCl (aq.), followed by concentrated. The concentrated residue was extracted with DCM (15 L) after pH adjusted to about 3. The organic layer was concentrated and added into MTBE (40 L) for product precipitation. The precipitated product was separated by filtration and washed with MTBE (2×20 L). Yield: 1.48 kg Example 4

Preparation of GlyGlyAsn(Trt)GlyOtBu (S2M4) (SEQ ID NO: 1)

The protected amino acid GlyOtBu.HCl (0.30 kg) and FmocAsn(Trt)OH (1 kg) and HOBt (0.24 kg) were stirred in DCM (5 L). NMM (0.19 L) and EDCI (0.48 kg) was added to the mixture. The reaction mixture was reacted for 3 h to give the DCM solution of intermediate (S2M1). DBU (1 L) was added to the DCM solution of intermediate (S2M1) and reacted for 3 h. The reaction mixture was washed with water (3×3.5 L) to give DCM solution of intermediate (S2M2, about 5 L). Protected amino acid FmocGlyGlyOH (0.59 kg) and HOBT (0.14 kg) were added to the DCM solution of intermediate (S2M2) and EDCI (0.48 kg) was added. The reaction mixture was reacted for 6 h to give solution of intermediate (S2M3). DBU (1 L) was added to the solution of intermediate (S2M3) and reacted for 1 h. The reaction mixture was washed with water (3×15 L). The organic layer was concentrated and the product was precipitated out by adding MTBE (40 L). The precipitated product was separated by filtration and washed with MTBE (2×7 L). Yield 0.71 kg Example 5

Preparation of FmocGlyGlyGlyGlyAsnGlyOH (S2) (SEQ ID NO: 2)

The compounds from Example 4 (1.00 Kg) and protected amino acid FmocGlyGlyOH (0.59 kg) were dissolved in mixed solvent of DMF/DCM (3 L/10 L) and HOBt (0.14 kg) was added. EDCl (0.35 kg) was added to the mixture and reacted for 16 h. The intermediate (S2M5) was precipitated out by adding mixed solvent of n-heptane/MTBE (30 L/30 L)

and separated by filtration, then washed with MTBE (2×5 L). The precipitated intermediate (S2M5) was stirred in mixed solvents of water (0.39 L), TIS (0.39 L) and TFA (14.8 L) and reacted for 2 h. The reaction mixture was precipitated out by adding MTBE (80 L) and separated by filtration, washed with MTBE (2×8 L). Yield: 0.72 kg Example 6

Preparation of HCl.IleProOBn (S3M2)

The protected amino acids ProOBn.HCl (1.00 kg) and BocIleOH 0.5 H2O (1.04 Kg) were dissolved in DCM (6 L) and HOBt (0.56 kg) was added. NMM (0.84 L) and EDCI (1.19 kg) were added and the reaction was allowed to stir for 4 h. The reaction mixture was washed with water (total 9 L) and NaHCO3 (aq. 3 L) followed by cocentrated to give the intermediate (S3M1, Foam). The intermediate (S3M1) was dissolved into HCl(g)/IPA (about 13%, 3 L) and stirring continued for another 3 h. The product was precipitated out by solvent replacement with n-Heptane and adding MTBE (20 L). The precipitated product was separated by filtration, washed with MTBE (total 16 L). Yield: 1.4 kg Example 7

Preparation of FmocGlu(tBu)Glu(tBu)IleProOBn (S3M7) (SEQ ID NO: 3)

The compounds from Example 6 (1.00 Kg), protected amino acid FmocGlu(tBu)OH (0.87 kg) and HOBt (0.28 kg) were dissolved in DCM (7 L). NMM (0.35 L) and EDCI (0.60 kg) were added and the reaction was allowed to stir for 1 h to give DCM solution of intermediate (S3M3, about 7 L). DBU (0.47 L) was added into the DCM solution of intermediate (S3M3) and was allowed react for 1 h. The reaction was washed with water (total 9 L) and 5% Na2CO3 (aq. 3 L) to give DCM solution of intermediate (S3M4, about 7 L). The DCM solution of intermediate (S3M4) was mixed with protected amino acid FmocGlu(tBu)OH (0.86 kg) and HOBt (0.28 kg). EDCI (0.60 kg) was added and was allowed to react for 1 h to give DCM solution of intermediate (S3M5, about 7 L). DBU (0.47 L) was added into the DCM solution of intermediate (S3M5) and was allowed react for 1 h. The reaction mixture was washed with water (total 9 L) and 5% Na2CO3 (aq. 3 L) to give DCM solution of intermediate (S3M6, about 7 L). The DCM solution of intermediate (S3M6) was mixed with protected amino acid FmocPheOH (0.78 kg) and HOBt (0.28 kg). EDCI (0.60 kg) was added and was allowed to react for 1 h. The product was precipitated out by slowly adding MTBE (20 L) and was separated by filtration and washed with MTBE (3 L). The intermediate (S3M1) was dissolved into HCl(g)/IPA (about 13%, 3 L) and stirring continued for another 3 h. The product was precipitated out by solvent replacement with n-Heptane and adding MTBE (20 L). The precipitated product was separated by filtration, washed with MTBE (total 16 L). Yield: 1.84 kg Example 8

Preparation of AspPheGlu(tBu)Glu(tBu)IleProOBn (S3) (SEQ ID NO: 5)

The compound from Example 7 (1.00 Kg) was dissolved in DCM (10 L). DBU (0.22 L) was added and the reaction was allowed to react for another 1 h. The reaction mixture was washed with water (total 9 L) and 5% Na2CO3 (aq. 3 L) to give DCM solution of intermediate (S3M8, about 10 L). The DCM solution of intermediate (S3M8) was mixed with protected amino acid FmocAsp(tBu)OH (0.38 kg) and HOBt (0.13 kg). EDCI (0.27 kg) was added into the mixture and was allowed to react for 1 h to give DCM solution of intermediate (S3M9, about 10 L). DBU (0.22 L) was added into the DCM solution of intermediate (S3M9) and was allowed to react for another 1 h. The reaction mixture was washed with water (total 9 L) and 5% Na2CO3 (aq. 3 L). The product was precipitated out by slowly adding mixed solvent of n-Heptane/MTBE=1/1(35 L). The precipitated product was separated by filtration and washed with MTBE (6 L). Yield: 0.90 kg Example 9

Preparation of Glu(tBu)Tyr(tBu)LeuOtBu (S4M4)

The protected amino acids FmocTyr(tBu)OH (1.00 kg) and LeuOtBu.HCl (0.50 kg) were dissolved in DCM (8 L) and HOBt (0.33 kg) was added. DIEA (0.44 L) and EDCI (0.50 kg) were added and the reaction mixture was stirred for 2 h. DEA (2.27 L) was added and the reaction mixture was allowed to react for 2 h. The reaction mixture was neutralized by 1N HCl (aq.) and the resulting mixture was further washed by 5% Na2CO3 (aq. about 5.3 L) to give DCM solution of intermediate (S4M2, about 8 L). The DCM solution of intermediate (S4M2) was mixed with protected amino acid FmocGlu(tBu)OH (0.93 kg) and HOBt (0.32 kg). EDCI (0.63 kg) was added and the reaction mixture was allowed react for 2 h. DEA (2.27 L) was added to the reaction and allowed to react for another 3 h followed by washed with water (2×15 L). The organic layer was diluted by n-Heptane (30 L) followed by concentrated to about 25 L and the product was precipitated out by adding another parts of n-Heptane (5 L). The precipitated product was separated by filtration and washed with n-Heptane (10 L). Yield: 1.09 kg Example 10

Preparation of Glu(tBu)Glu(tBu)Tyr(tBu)LeuOtBu (S4) (SEQ ID NO: 6)

The compounds from Example 9 (1.00 Kg), protected amino acid FmocGlu(tBu)OH (0.72 kg) and HOBt (0.25 kg) were dissolved in DCM (8 L). EDCI (0.39 kg) was added and the reaction mixture was allowed to react for 2 h. DEA (1.77 L) was added and the reaction mixture was allowed to react for 3 h followed by washed with water (2×15 L). The organic layer was diluted by n-Heptane (30 L) followed by concentrated to about 25 L and the product was precipitated out by adding another parts of n-Heptane (5 L). The precipitated product was separated by filtration and washed with n-Heptane (10 L). Yield: 1.11 kg Example 11

Preparation of GlyGlyGlyGlyAsnGlyAsp(tBu)PheGlu(tBu)Glu(tBu)IleProOBn (M2) (SEQ ID NO: 7)

The compounds from Example 8 (1.00 Kg) and Example 5 (0.70 kg) were dissolved in DMSO (7 L) and HOBt (0.16 kg)

was added. EDCl (0.48 kg) was added and the reaction mixture was allowed stirring for another 1 h, then Piperidine (1 L) was added and the reaction was allowed stirring for another 2 h. The product was precipitated out by adding water (35 L). The precipitated product was separated by filtration and washed with water (2×10 L) and MTBE (3×10 L). Yield: 1.26 kg Example 12

Preparation of Boc-D-PheProArgProGlyGlyGlyGlyAsnGlyAsp(tBu)PheGlu(tBu)Glu(tBu)IleProOH (M4)

The compounds from Example 11 (1.00 Kg) and Example 3 (0.49 kg) were dissolved in DMSO (5.5 L) and HOBt (0.12 kg) was added. EDCl (0.16 kg) was added and the reaction mixture was allowed stirring for another 1 h. The intermediate (M3) was precipitated out by adding water (28 L) and separated by filtration and washed with water (2×12 L). The precipitated intermediate (M3) was stirred in 66% ACN (aq, about 20 L). Pd/C (10%, 0.13 Kg) was added into the mixture, followed by Hydrogen gas was introduced and reaction was allowed to agitate vigorously for 16 h. The reaction mixture was filtered and the product in the filtrate was precipitated out by azeotrope water with ACN to dryness. Yield: 1.04 Kg Example 13

Preparation of: D-PheProArgProGlyGlyGlyGlyAsnGlyAspPheGluGluIleProGluGluTyrLeuOH.nTFA (Crude Bivalirudin)

The compounds from Example 12 (1.00 Kg) and Example 10 (0.42 kg) were dissolved in DMSO (5.8 L) and HOBt (0.08 kg) was added. EDCl (0.15 kg) was added and the reaction mixture was allowed stirring continued for another 1 h. The intermediate (M5) was precipitated out by adding water (24 L) and was separated by filtration and washed with water (2×6 L). The precipitated intermediate (M5) was dissolved in mixed solvents of water (0.08 L), TIS (0.33 L) and TFA (7.92 L) and the mixture was allowed to react for 1 h. The product was precipitated out by slowly adding MTBE (29.2 L) and was separated by filtration, washed with MTBE (2×8.3 L) and THF (2×8.3 L). Yield: 1.12 kg While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. It is intended, therefore, that the invention be defined by the scope of the claims which follow and that such claims be interpreted as broadly as is reasonable.

What is claimed:

1. A process for the preparation of Bivalirudin comprising the steps of:
   a) condensing the segment AspPheGlu(tBu)Glu(tBu)IleProOBn (SEQ ID NO: 5) (S3) and the segment FmocGlyGlyGlyGlyAsnGlyOH (SEQ ID NO: 2) (S2) in a first organic solvent;
   b) deprotecting the product of step a);
   c) condensing the product of step b) and the segment Boc-D-PheProArg(HCl)ProOH (S1) in a second organic solvent;
   d) deprotecting the benzyl group of the product of step c);
   e) condensing the product of step d) and the segment Glu(tBu)Glu(tBu)Tyr(tBu)LeuOtBu (SEQ ID NO: 6) (S4) in a third organic solvent; and
   f) deprotecting the product of step e) to obtain Bivalirudin.

2. The process according to claim 1, wherein the first, second and third organic solvents are independently selected from DCM, DMF, and DMSO.

3. The process according to claim 1, wherein the deprotection of the product of step b) is performed by using a nucleophilic base.

4. The process according to claim 1, wherein the deprotection of the product of step d) is performed by hydrogenation in presence of a catalyst.

5. The process according to claim 1, wherein the deprotection of the product of step f) is performed by reacting with a mixture of TFA/TIS/$H_2O$ to obtain Bivalirudin.

6. A process for the preparation of Bivalirudin comprising the steps of:
   a) condensing the segment AspPheGlu(tBu)Glu(tBu)IleProOBn (SEQ ID NO: 5) (S3) and the segment FmocGlyGlyGlyGlyAsnGlyOH (SEQ ID NO: 2) (S2) in a first organic solvent;
   b) deprotecting the product of step a);
   c) condensing the product of step b) and the segment Boc-D-PheProArg(HCl)ProOH (S1) in a second organic solvent;
   d) deprotecting the benzyl group of the product of step c);
   e) condensing the product of step d) and the segment Glu(tBu)Glu(tBu)Tyr(tBu)LeuOtBu (SEQ ID NO: 6) (S4) in a third organic solvent; and
   f) deprotecting the product of step e) to obtain Bivalirudin;
   wherein the first, second and third organic solvents are independently selected from DCM, DMF, and DMSO; the deprotection of the product of step f) is performed by reacting with a mixture of TFA/TIS/$H_2O$ to obtain Bivalirudin.

7. The process according to claim 1, wherein the deprotection of the product of step d) is performed by hydrogenation in the presence of a catalyst.

* * * * *

SEQUENCE LISTING

```
<160> NUMBER OF SEQ ID NOS: 8

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Asn Gly
1

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Gly Gly Asn Gly
1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3
```

```
Glu Glu Ile Pro
1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Phe Glu Glu Ile Pro
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Phe Glu Glu Ile Pro
1               5

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Glu Glu Tyr Leu
1

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Gly Gly Gly Asn Gly Asp Phe Glu Glu Ile Pro
1               5                   10

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Phe Pro Arg Pro Gly Gly Gly Gly Asn Gly Asp Phe Glu Glu Ile Pro
1               5                   10                  15

Glu Glu Tyr Leu
            20
```